United States Patent [19]

Pizzino

[11] Patent Number: 4,610,666
[45] Date of Patent: Sep. 9, 1986

[54] DUAL SYRINGE

[76] Inventor: Joanne L. Pizzino, 1426 Sugar Knoll, Akron, Ohio 44313

[21] Appl. No.: 747,935

[22] Filed: Jun. 24, 1985

[51] Int. Cl.$^4$ .............................................. A61M 5/08
[52] U.S. Cl. .................................... 604/191; 604/249
[58] Field of Search ............... 604/191, 236, 249, 246, 604/227, 238, 187, 81, 82

[56] References Cited

U.S. PATENT DOCUMENTS

| | | | |
|---|---|---|---|
| 1,672,114 | 6/1928 | Crow | 604/249 |
| 1,944,553 | 1/1934 | Freund | 604/249 |
| 4,109,653 | 8/1978 | Kozam et al. | 604/191 |
| 4,137,917 | 2/1979 | Cohen | 604/190 |
| 4,252,159 | 2/1981 | Maki | 604/208 |
| 4,367,737 | 1/1983 | Kozam et al. | 604/191 |
| 4,381,778 | 5/1983 | Kozam et al. | 604/191 |

Primary Examiner—John D. Yasko
Attorney, Agent, or Firm—Oldham, Oldham & Weber Co.

[57] ABSTRACT

Disclosed is a syringe having two or more barrels for injection of two or more liquids into a patient in predetermined sequence. The syringe includes a valve, either a slide valve or a rotary valve, which places the barrels one at a time in predetermined sequence in communication in the needle of the syringe. Preferably the syringe is prefilled with the desired injectable liquids and the valve is preset so that the barrel containing the first liquid to be dispensed is in communication in the needle.

17 Claims, 6 Drawing Figures

4,610,666

DUAL SYRINGE

TECHNICAL FIELD

This invention relates to syringes and particularly to syringes for medical use. More particularly, this invention relates to a novel syringe having two or more barrels which permits the injection of a plurality of liquids into a patient in a predetermined sequence.

BACKGROUND ART

Therapy involving the adminstration of intravenous solutions to patients is in wide-spread use. The solution may be administered continuously over a long period of time, as for example a glucose solution or an antibiotic in solution; or may be administered periodically (say every 4, 6 or 8 hours), as for example in the case of certain antibiotics. In either of these situations it is necessary for the vein to remain accessible and patent (that is, open) without the necessity of multiple venous punctures. It is common practice to insert into the patient's vein a needle having a hub and an adapter, commonly known as a heparin lock, thereon. The heparin lock is simply a piece of self-sealing rubber or other elastomer removably attached to the hub of the needle. To prevent blood clotting in the needle, i.e. to maintain patency, saline and heparin solutions must be injected in that order into the needle from separate syringes, approximately once every 6 to 8 hours. Typically these solutions are injected through the heparin lock.

It is established medical practice to confirm proper placement of the needle into the patient's vein, to flush the needle, and to maintain patency. To confirm proper placement, one inserts the needle of a saline-filled syringe through the heparin lock into the needle and raises the plunger of the syringe so as to withdraw a small amount of blood from the patient's vein into the syringe. This is commonly known as a blood return. Thereafter, to flush the needle, saline solution is injected from the syringe through the needle into the patient. Finally, to maintain patency, it is necessary to inject heparin periodically, say once every 6 to 8 hours. This, of course, requires a second syringe, one which has been filled with a heparin solution.

A typical procedure for injecting the saline and heparin solution into a patient is as follows: Step one, the person administering the injection first withdraws the saline solution from a vial into the syringe. Step two, the person injects this solution into the patient. Step three, the person takes a second syringe and needle and withdraws the heparin solution from a vial. Step four, the person injects this solution into the patient.

This procedure is typical of the procedure that would be followed for injection of any two liquids in predetermined sequence into a patient.

It will be appreciated that there are chances for error, both in measuring the amount of each ingredient to be administered and in administering the substances in the correct sequence. For example, in administering heparin, the saline solution is always administered first, followed by the heparin solution.

Because of the several steps required and the use of multiple dose vials for saline, there is a possibility of contamination. There is also a possibility of medication error.

Saline and heparin solutions have recently become commercially available in cartridge form. Each cartridge contains the required dosage. Although this eliminates the possibility for dosage error, the possibility of incorrect order of insertion remains. To use cartridges of saline and heparin solutions (each of which includes its own needle), it is necessary to insert each of the cartridges in turn into a cartridge holder (which includes a plunger), the saline cartridge being inserted first, and to follow the same four steps which have been previously given for injecting the saline and heparin solutions into the patient.

In certain other situations two liquids must be injected into a patient either mixed or separately in either order. One such situation is simultaneous administration of two different types of insulin (regular normal and long acting, for example), to a diabetic patient. Insulin injection is complicated by the fact that dosage requirements vary from patient to patient and even for the same patient. One procedure presently used is as follows: the person administering the insulin injects into the first multiple dose vial (Vial No. 1), which contains one kind of insulin, a volume of air equal to the amount of insulin to be withdrawn from that vial. Then he/she withdraws the required amount of insulin from Vial No. 1 into the syringe. Then, after removing the needle from Vial No. 1, the person further withdraws the plunger to fill the syringe with the proper amount of air for injection into Vial No. 2, which contains a second type of insulin. The person inserts the syringe into Vial No. 2 and carefully expel the air in the syringe into Vial No. 2 taking care not to expel any solution of the syringe into Vial No. 2. Then the person withdraws the plunger, which causes the solution from Vial No. 2 to be drawn into the syringe. The syringe is then ready for injection. As one can appreciate, it is very difficult to expel the required amount of air into Vial No. 2 without also expelling a small amount of insulin from Vial No. 1. If some insulin from Vial No. 1 is expelled, of course some insulin from Vial No. 1 will be introduced into multiple dose Vial No. 2, so that Vial No. 2 no longer contains a pure solution of insulin of the second type.

DISCLOSURE OF INVENTION

It is an object of this invention to provide a multiple barrel syringe which reduces from four steps to one step the number of steps required to inject two different liquids into a patient, in predetermined sequence.

Another object of this invention is to minimize the possibility of incorrect sequence of delivery.

Still another object of this invention is to minimize the possibility of incorrect dosage.

It is still another object of this invention to eliminate the the risk of undesirable mixing which may result when two different injectable liquids are injected with the same syringe.

These and other objects are accomplished by providing a novel, multiple barrel syringe for injecting a plurality of liquids into a patient in predetermined sequence. This syringe comprises:

a body;

a plurality of barrels in this body, each of the barrels being adapted to contain an injectable liquid;

a plunger in each barrel for injection of said liquid;

a manually operable valve in the syringe body for controlling the dispensing of the respective liquids from the barrels, said valve being arranged so that the liquids are dispensed one at a time in predetermined sequence;

a cavity in the body on the outlet side of the valve for receiving the liquid;

and a needle in communication with the cavity for injecting the liquids into a patient.

BRIEF DESCRIPTION OF DRAWINGS

Figure 2:
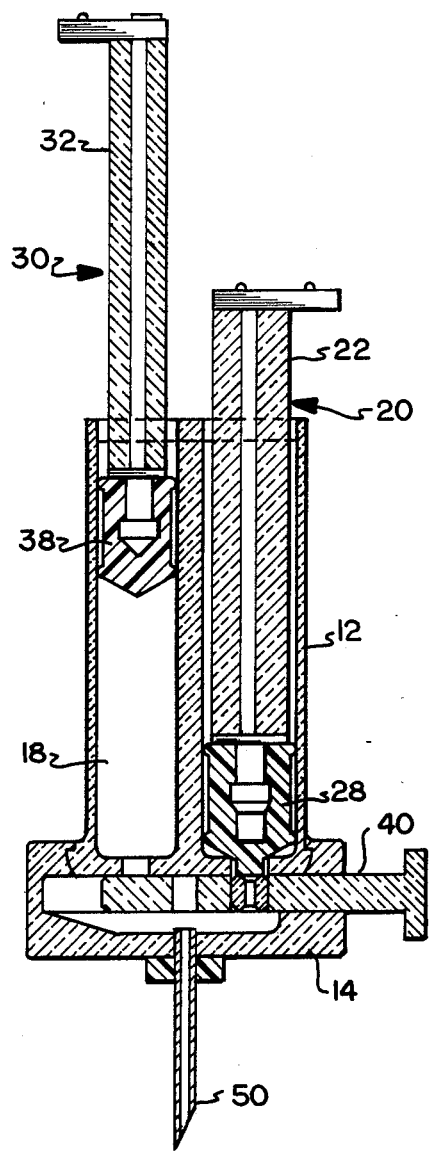
Figure 1:
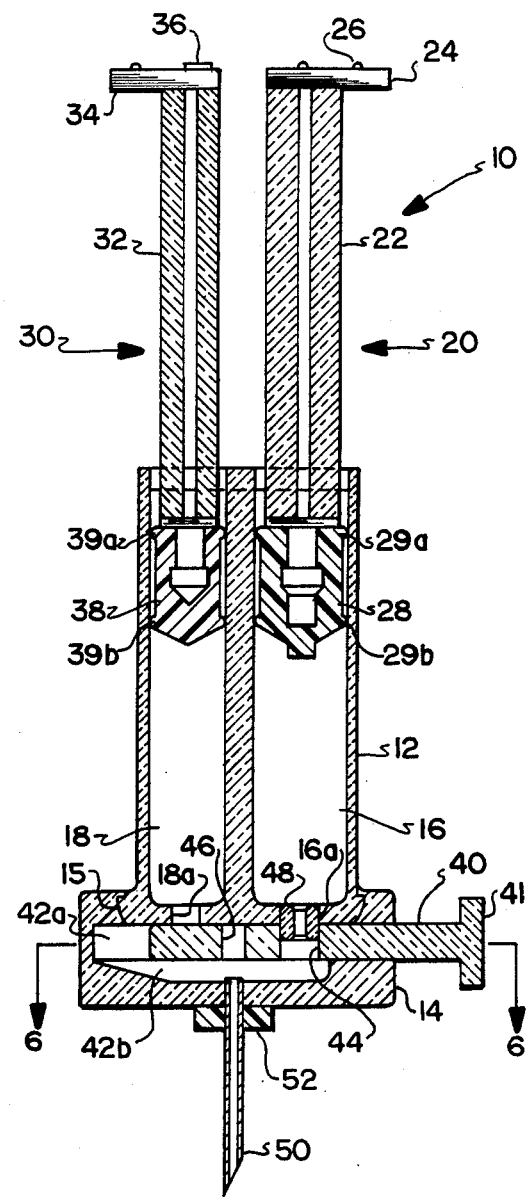

IN THE DRAWINGS:

FIG. 1 is a vertical sectional view of a syringe according to the preferred embodiment of this invention, showing the syringe as it would appear when delivered to the user.

FIG. 2 is a vertical sectional view of the syringe of FIG. 1 showing the syringe after one of the barrels has been emptied, with the slide valve still in the position for dispensing from this barrel.

Figure 3:
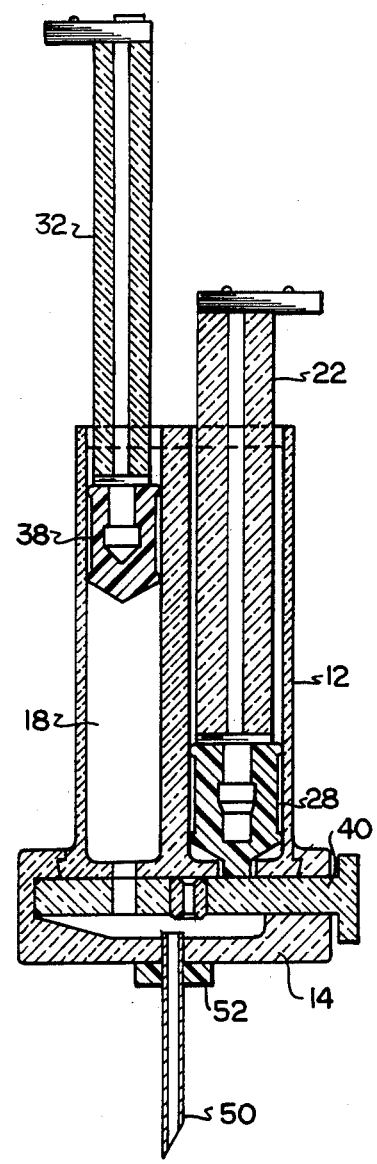

FIG. 3 is a vertical sectional view of the syringe of FIG. 1, showing the syringe as it appears when the second barrel is about to begin.

Figure 4:
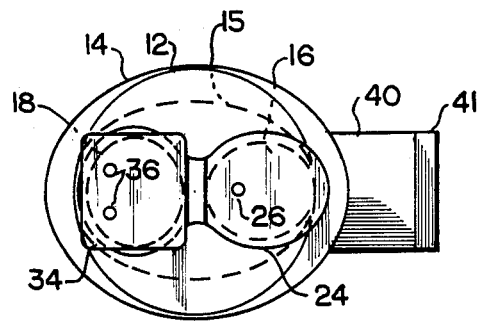

FIG. 4 is a top plan view of the syringe of this invention.

Figure 5:
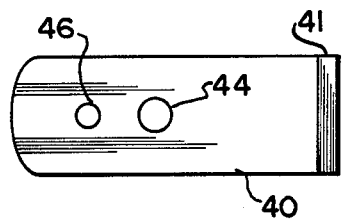

FIG. 5 is a plan view of the slide valve in the embodiment of FIG. 1.

Figure 6:
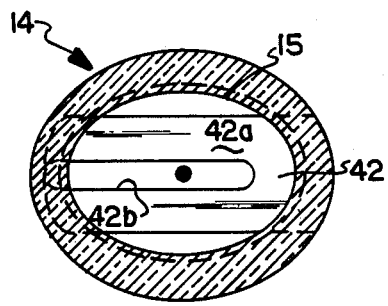

FIG. 6 is a top plan view of the valve body portion of the syringe of this invention with the slide valve removed.

BEST MODE FOR CARRYING OUT THE INVENTION

This invention will now be described in detail with respect to the preferred embodiment. This preferred embodiment is a single use syringe which is prefilled with saline and heparin solutions. Such a syringe is particularly useful in maintaining patency of an needle used in administering intravenous solutions. The preferred syringe has two barrels and, therefore, may be referred to as a dual syringe. It will be understood that the invention is more broadly useful in any situation where two or more injectable liquids are to be injected into a patient, and is especially useful where the liquids must be injected in a predetermined sequence.

The preferred embodiment will be described with particular reference to FIGS. 1-6. Refering now to FIG. 1, 10 indicates generally the preferred syringe according to this invention. Syringe 10 includes a clear plastic body having a generally cylindrical main body portion 12 of oval cross section and a clear plastic valve body section 14, also of oval cross section but having a major axis which is greater than the major axis of the main body portion 12. The two body portions are joined together, e.g. by cementing, along mating surfaces 15. These mating surfaces are curved surfaces of revolution. The main body surface is generally convex and the valve body surface is correspondingly concave.

The main body portion 12 has a plurality of barrels, each of which is adapted to contain an injectable liquid. In the preferred embodiment shown, there are two barrels 16 and 18, the first barrel 16 being of round cross section and prefilled with a sterile aqueous saline solution, and a second barrel 18 being of oval cross section and prefilled with a solution of heparin. Barrels 16, 18 have restricted openings 16a, 18a respectively at the bottom thereof for outflow of the solutions from the barrels.

Each of the barrels 16 and 18 has a plunger therein for controlling the dispensing of liquid from the barrel. Barrel 16 has a plunger 20 which includes a hollow, rigid, clear plastic shaft 22, a round thumb pad 24 with raised markings 26 at the upper end of the shaft, and a flexible seal 28, preferably of flexible clear plastic material, at the lower end of the shaft. Seal 28 has a tip 28a on its front (or distal) end for a purpose to be described hereafter. Seal 28 has a pair of lateral projections 29a, 29b which maintain sealing contact with the inside wall of barrel 16. Seal 28 is generally of round cross section to conform with the shape of barrel 16. Similarly, the second barrel 18 has a plunger 30 having a rigid, hollow, clear plastic shaft 32, a square thumb pad 34 with raised markings 36 at the upper end of the shaft and a seal 38 with projections 39, 39a at the lower end of the shaft. Raised markings 36 on square thumb pad 34, are different from the markings 26 on round thumb pad 24. The difference in thumb pad shapes and the presence of different raised markings makes it possible for the user of the syringe to determine by feel, without looking at the syringe, which of the two thumb pads he/she is touching. This is useful so that the user of the syringe will not attempt to dispense the respective solutions in barrels 16 and 18 in incorrect sequence. The markings 26 and 36 may be either conventional Braille markings or any other raised markings which are readily distinguishable from each other by feel. The markings can be omitted, particularly if the thumb pads are of different shapes, or the thumb pads can be of the same shape, particularly if they have raised markings which differ from each other. These features, although optional, are very handy to enable the user of the syringe to distinguish quickly which thumb pad he/she is touching.

Syringe 10 has a manually operable valve 40 which is disposed in cavity 42 in the valve body portion 14 of syringe 10. Valve 40 includes a thumb pad 41 which is on the outside of valve body section 14. Cavity 42 includes a horizontal slotted portion 42a for valve 40 and a free space 42b on the outlet side of valve 40 (i.e. below slotted portion 42a) to receive the solutions from barrel 16 and 18 after they pass through the valve 40. Valve 40 includes a pair of openings 44, 46, both extending from one side of valve 40 to the other in the thickness direction. Valve 40 is slidable between two positions as may be seen in FIGS. 1 and 3 respectively. In the first position, shown in FIG. 1, opening 44 is aligned with the outlet opening 16a of barrel 16, so that the solution in barrel 16 may flow into the cavity 42. Meanwhile the outlet of barrel 18 is closed. Opening 44 is of larger diameter of opening 46 and has an annular locking pin 48 which has a hole through its center to permit passage of fluid from barrel 16 into cavity 42.

Locking pin 48 is in the raised position shown in FIG. 1 at the time syringe 10 is delivered to the user. This prevents any movement of slide valve 40. When the dispensing of injectable liquid from barrel 16 is nearly complete (i.e., when plunger 20 approaches its lowermost position), tip 28a engages locking pin 48, moving the locking pin 48 down to the position shown in FIG. 2. In this position, valve 40 can be slid to its second position, shown in FIG. 3, in which opening 46 is aligned with the outlet opening 18a of barrel 18 to permit dispensing of fluid from this barrel, and the outlet of barrel 16 is closed. As has been seen, only one barrel 16 or 18 at a time is in communication with the cavity 42 on the outlet side of valve 40.

A needle 50 extends outwardly from the bottom of valve body portion 14 of syringe 10. This needle is hollow providing a passageway for injection of liquids from the syringe into the patient. This passageway is in communication with cavity 42. An annular rubber needle hub 52 which is preassembled with the needle, surrounds needle 50 and is in abuting relationship with the bottom of valve body portion 14.

Refilled syringe 10 should be packaged in a sterile package for delivery to the user.

Operation of the syringe 20 will now be described with particular reference to injecting of saline solution followed by heparin solution from a pre-filled syringe through an intravenous needle having a hub at one end.

First, a heparin lock, which may be conventional, is placed on the hub of the intravenous needle. A heparin lock is simply a head of self-sealing elastomer. After the heparin lock has been inserted into the patient's vein, needle 50 of syringe 10 is inserted into the heparin lock, and plunger 20 is raised slightly to draw a small quantity of blood into cavity 42. This follows current medical practice and is done simply to indicate proper placement of the intravenous needle. Next, with the valve 40 and syringe 10 in the position shown in FIG. 1, the user of the syringe depresses plunger 20 by pushing on thumb pad 24. The saline solution in valve 16 passes through valve opening 44, cavity 42 and needle 50 into the vein of the patient. As injection of saline solution is completed, tip 28a of plunger 20 engages locking pin 48 so that locking pin 48 moves from its initial position shown in FIG. 1 to the position shown in FIG. 2, which will permit movement of valve 40. When injection of the saline solution is complete, the plunger 20 and valve 40 will be in the position shown in FIG. 2. Then valve 40 is slid to the position shown in FIG. 3 by pressing on the thumb pad 41. Then the user presses plunger 30 by pressing down on thumb pad 34 in order to dispense the heparin solution contained in barrel 18. The solution in this barrel flows successively through valve opening 46, cavity 42, and needle 50 into the vein of the patient. Needle 50 is withdrawn from the heparin lock when dispensing of heparin solution from barrel 18 is completed. The intravenous needle and heparin lock is left in the patient's vein for injection of further quantities of glucose I.V. solution and future doses of saline and heparin solutions.

Various modifications in both the syringe itself and in the method of its use are possible without departing from this invention. For example, the syringe is of general utility in any situation where two or more liquids are to be injected into a patient. It is particularly useful when the liquids must be injected in predetermined sequence. Even when two or more liquids may be injected in any order or as a mixture, the syringe of this invention represents an improvement over present practice. For example, the syringe of this invention may be used to inject two different types of insulin. A syringe for this purpose is not prefilled. It is not practical to prefill a syringe to be used for insulin injections, because the quantity of insulin a patient requires may vary from day to day.

When the syringe 10 is to be used for injecting two types of insulin, plungers 20 and 30 are down as far as they can go (i.e. in the position in which plunger 20 is shown in FIGS. 2 and 3) and the syringe is dry, (i.e. not prefilled with the liquids to be injected). Also, the slide valve 40 is initially in the position shown in FIG. 3, i.e., so as to place barrel 18 in communication with cavity 42. Barrels 18 and 16 are filled in that order, i.e., in the reverse order of that used for dispensing injectable liquids. The user raises plunger 30 to draw the required amount of the second injectable liquid into barrel 18. When barrel 18 has been filled, the user moves slide valve 40 to the position shown in FIGS. 1 and 2, then raises plunger 20 to draw the required amount of first injectable liquid (say normal insulin) into barrel 16. Syringe is then ready for dispensing injectable liquids first from barrel 16, then from barrel 18. For insulin injections, the user will insert needle 50 subcutaneously into the patient, withdraw one plunger slightly to confirm that the needle has not entered a blood vessel, then will dispense the contents of barrels 16 and 18. Locking pin 48 may be omitted entirely when the syringe is to be used for insulin injections.

Syringe construction and injection procedures described above may be used in other situations where two or more liquids are to be injected and no particular sequence of injection is required.

The patient may be either a human or other warm blooded animal. The injectable liquids are usually solutions although they do not have to be. The transparent materials herein described are preferred for esthetic reasons although other materials can be used. The plunger seals 28 and 38 should be elastomeric for proper sealing and the other parts (e.g., syringe body portions 12 and 14, plungers 20 and 30, and slide valve 40) should be rigid.

Syringe 10 can be used for any type of medically recognized injection, e.g., intravenous (which has been described above), subcutaneous, or intramuscular.

The syringe 10 may have more than two barrels; the number of barrels is determined strictly by the number of liquids to be injected. For example, the syringe may have four barrels. The syringe may have a rotary valve instead of a slide valve. Barrels 16 and 18 may be either the same shape or of different shapes as shown. Similarly, thumb pads 24 and 34 may be of either the same or different shapes, and raised markings 26 and 36 on the thumb pads may be either present or absent. However, it is highly desirable for safety reasons either to provide thumb pads of different shapes or to provide different raised markings which can be distinguished by feel, so that the user can use the syringe by feel without having to look at it in order to determine the proper sequence.

Plungers 20 and 30 (or barrels 16 and 18 if desired) may be color coded so that they can be quickly distinguished visually. Also, the contents of each barrel (e.g. "saline" and "heparin") may be marked on the respective barrels by suitable means. Syringes according to this invention which are not prefilled may be calibrated either by volume (cubic centimeters) or in medication units to show quantities of medication. This is highly useful, in fact, necessary for syringes used for insulin injection.

Syringes of the present invention and their use offer a number of advantages which are not obtainable in present practice. First, only a single step and a single syringe are required to inject two or more liquids, in contrast to at least four steps and two syringes which are required under present practice for administering two injectable liquids. Second, the risk of contamination is greatly decreased. Third, the possibility of incorrect dosage is minimized. Fourth, the possibility of incorrect sequence of delivery is eliminated.

Even in situations where the syringe is not prefilled and sequence of delivery is not important, the present syringe offers some advantages. First, risk of contamination is decreased. A single syringe can be used to administer more than one injectable liquid without contaminating any of the bodies of liquid from which the syringe is filled. Secondly, the possibility of incorrect dosage is reduced. Potential inaccuracies of dosage which are inherent when two or more medications are filled into the same syringe barrel are eliminated.

While in accordance with the patent statutes, a preferred embodiment and best mode has been presented, the scope of the invention is not limited thereto, but rather is measured by the scope of the attached claims.

What is claimed is:

1. A syringe for injecting a plurality of liquids into a patient in predetermined sequence, said syringe comprising:

a main body portion having a plurality of barrels therein, each of said barrels being adapted to contain an injectable liquid;

a plunger in each barrel for injection of said liquid;

a valve body portion below said main body portion, said valve body portion having a manually operable valve therein and a free space on the outlet side of said valve for receiving said injectable liquids, said valve being movable successively to a plurality of positions so as to place each of said barrels in communication with said free space in a predetermined sequence;

means for preventing movement of said valve in a sequence other than the predetermined sequence, whereby dispensing of liquids in an incorrect order is prevented; and a needle in communication with said free space for injecting said liquids into a patient.

2. A syringe according to claim 1 having at least two barrels filled with different liquids.

3. A syringe according to claim 1 in which there are two barrels.

4. A syringe according to claim 3 in which said valve is a slide valve, slidable between two positions, the first position permitting dispensing of medication from the first barrel and the second position permitting dispensing of medication from the second barrel.

5. A syringe according to claim 4 including a locking pin, said locking pin being positioned initially so as to prevent movement of said valve and being moved at the completion of dispensing liquid from the first barrel to a position which permits movement of said valve.

6. A syringe according to claim 1 in which each of said plungers has a thumb pad at the top thereof and at least one of said thumb pads has raised markings which are distinguishable by touch from the other thumb pad including any markings thereon.

7. A syringe for injecting a pair of liquids into a patient in predetermined sequence, said syringe comprising:

a body;

two barrels in said body, each of said barrels being adapted to contain an injectable liquid;

a plunger in each barrel for injection of said liquid;

a manually operable slide valve in said body for controlling the dispensing of the respective liquids from said barrels, said valve being slidable between two positions, the first position permitting dispensing of medication from the first barrel and the second position permitting dispensing of medication from the second barrel;

a locking pin, said locking pin being positioned initially so as to prevent movement of said valve and being moved at the completion of dispensing liquid from the first barrel to a position which permits movement of said valve;

a cavity in said body on the outlet side of said valve for receiving said liquids; and a needle in communication with said cavity for injecting said liquids into a patient.

8. A syringe according to claim 1 in which only one barrel at a time is in communication with said free space.

9. A syringe according to claim 1 in which said means for preventing movement of said valve in a sequence other than the predetermined sequence are locking means.

10. A syringe according to claim 9 in which said locking means include a locking pin.

11. A syringe according to claim 1 in which said barrels are filled with different liquids.

12. A syringe according to claim 1 in which said valve is a slide valve.

13. A syringe according to claim 12 in which said slide valve has a plurality of openings extending therethrough.

14. A syringe according to claim 1 in which each of said barrels has a restricted outlet opening.

15. A syringe according to claim 1 in which said main body portion, said valve body portion and said needle are in fixed relationship with respect to each other.

16. A syringe for injecting a plurality of liquids into a patient in predetermined sequence, said syringe comprising:

a body having a plurality of barrels, each of which is adapted to contain an injectable liquid.

a plunger in each barrel for the injection of liquid;

a manually operated valve for controlling the dispensing of the respective liquids from said barrels, and a free space on the outlet side of said valve for receiving said liquids;

said valve being movable successively through a plurality of positions so as to place each of said barrels in communication with said free space in a predetermined sequence; and means for preventing movement of said valve in a sequence other than the predetermined sequence, whereby dispensing of liquids in an incorrect order is prevented.

17. A valve according claim 16, including a needle communicating with said free space.

* * * * *